US012649759B2

(12) United States Patent
Xia et al.

(10) Patent No.: US 12,649,759 B2
(45) Date of Patent: Jun. 9, 2026

(54) DEVICE AND METHOD FOR PREPARING SUCROSE-6-ESTER

(71) Applicant: ANHUI JINHE INDUSTRIAL CO., LTD., Chuzhou (CN)

(72) Inventors: Jiaxin Xia, Chuzhou (CN); Jingang Zhao, Chuzhou (CN); Zhengsong Zhang, Chuzhou (CN); Zhenghua Li, Chuzhou (CN); Congyong Zhang, Chuzhou (CN); Xuelian Zheng, Chuzhou (CN)

(73) Assignee: ANHUI JINHE INDUSTRIAL CO., LTD, Chuzhou City (CN)

( * ) Notice: Subject to any disclaimer, the term of this patent is extended or adjusted under 35 U.S.C. 154(b) by 652 days.

(21) Appl. No.: 18/018,615

(22) PCT Filed: Feb. 19, 2021

(86) PCT No.: PCT/CN2021/076811
§ 371 (c)(1),
(2) Date: Jan. 30, 2023

(87) PCT Pub. No.: WO2022/174382
PCT Pub. Date: Aug. 25, 2022

(65) Prior Publication Data
US 2023/0322836 A1     Oct. 12, 2023

(51) Int. Cl.
*C07H 13/04* (2006.01)
*B01D 3/00* (2006.01)
*B01D 5/00* (2006.01)

(52) U.S. Cl.
CPC ............ *C07H 13/04* (2013.01); *B01D 3/009* (2013.01); *B01D 5/0009* (2013.01); *B01D 5/006* (2013.01)

(58) Field of Classification Search
CPC ...... C07H 13/04; B01D 3/009; B01D 5/0009; B01D 5/006
USPC ........................................................ 536/119
See application file for complete search history.

(56) References Cited

U.S. PATENT DOCUMENTS 552,456 A * 12/1895 Theisen ................... C10G 9/42
2,484,445 A * 10/1949 Bibby ................... B01D 1/228
159/DIG. 4

FOREIGN PATENT DOCUMENTS

| CN | 101605804 A | 12/2009 |
| CN | 102639551 A | 8/2012 |
| CN | 104817597 A | 8/2015 |
| CN | 212315609 U | 1/2021 |
| EP | 776903 B1 | 1/2003 |
| WO | WO 2011/045565 * | 4/2011 |
| WO | 2019223485 A1 | 11/2019 |

OTHER PUBLICATIONS

PCT International Search Report (ISR)—PCT/CN2021/076811 (5 pages) (dated Nov. 18, 2021).
China Office Action, App No. 202180000303.1, dated Feb. 15, 2022.

* cited by examiner

*Primary Examiner* — Yih-Horng Shiao
(74) *Attorney, Agent, or Firm* — HEA Law PLLC; Darrin A. Auito

(57) ABSTRACT

Disclosed are a device and a method for preparing a sucrose-6-ester. The device includes a tank body, a heating pipe, an annular cooling apparatus, and a motor, wherein the annular cooling device and the heating pipe are arranged in the tank body in nested manner; the annular cooling apparatus includes a condensation inner wall, a condenser pipe, and a condensation outer wall that are arranged in nested manner; a distillation chamber is formed between the heating pipe and the tank body, a condensation chamber is formed between the heating pipe and the condensation outer wall, and a hollow portion of the condensation inner wall forms a reaction chamber; the heating pipe and the condensation inner wall are drove by the motor to rotate; the heating pipe is provided with a vapor outlet an evaporation residue channel is formed at an end of the heating pipe away from the feed inlet.

13 Claims, 3 Drawing Sheets

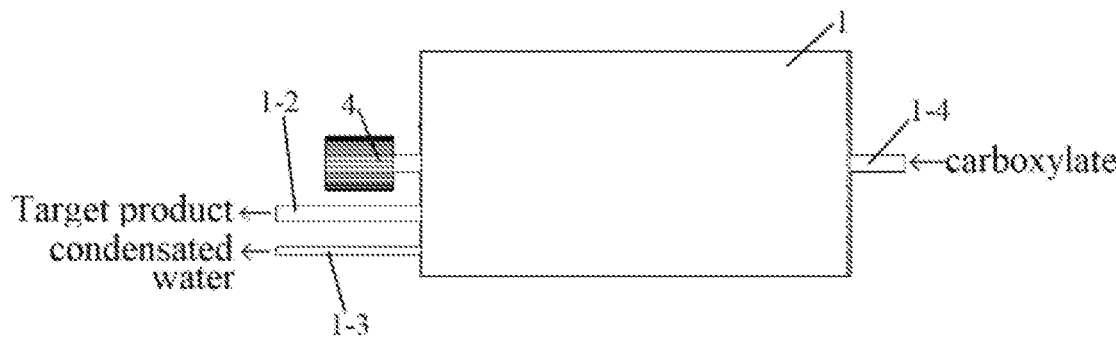

FIG. 5

| starting the motor and the annular cooling apparatus, setting the heating pipe to a preset temperature, and feeding a reaction solution from the feed inlet of the tank body, such that the reaction solution is separated into an evaporation residue and a water vapor in the distillation chamber; allowing the evaporation residue to flow into the evaporation residue channel; and allowing the water vapor to enter the condensation chamber from the vapor outlet and be condensated into liquid water, and allowing the liquid water to flow out through the condensated water outlet pipe, wherein the reaction solution comprises sucrose, an aprotic polar solvent, and an organotin esterification accelerator | S610 |

| subjecting the evaporation residue entering the reaction chamber through the evaporation residue channel to an esterification reaction with a carboxylic anhydride entering through the carboxylate feed pipe under preset conditions to obtain a sucrose-6-ester-containing solution | S620 |

DEVICE AND METHOD FOR PREPARING SUCROSE-6-ESTER

CROSS REFERENCE TO RELATED APPLICATION

The present application is a national stage application of International Patent Application No. PCT/CN2021/076811, filed on Feb. 19, 2021, which is incorporated by reference herein in its entirety.

TECHNICAL FIELD

The present disclosure belongs to the technical field of fine chemical production, and in particular relates to a device and a method for preparing a sucrose-6-ester.

BACKGROUND

Sucralose is a new sweetener with advantages such as high sweetness, no calories, high stability, and high safety, and has very promising market prospects. Sucralose-6-ester is an important intermediate for the production of sucralose.

In the prior art, a process for synthesizing a sucrose-6-ester mainly includes: mixing sucrose, an aprotic polar solvent, and an organotin esterification accelerator to obtain a first reaction mixture; removing the moisture from the first reaction mixture by contacting the first reaction mixture with a gas or solvent vapor capable of removing water for a specified period of time at a specific temperature and pressure to obtain a second reaction mixture; adding a carboxylic anhydride into the second reaction mixture to obtain a third reaction mixture; and subjecting the third reaction mixture to a reaction for sufficient time to obtain the sucrose-6-ester. This process requires the use of the gas or solvent vapor capable of removing water, which seriously affects the continuity of a sucrose-6-ester production process, prolongs the production cycle, and reduces the production efficiency. In addition, the consumption of a large amount of the gas or solvent capable of removing water greatly increases the production cost, and energy consumption.

It should be noted that the statements herein merely provide background information related to the present disclosure and do not necessarily constitute the prior art.

SUMMARY

In view of the above, present disclosure provides a device and a method for preparing a sucrose-6-ester, which make it possible to overcome the above problems or at least partially solve the problems.

According to at aspect of the present disclosure, provided is a device for preparing a sucrose-6-ester, including a tank body, a heating pipe, an annular cooling apparatus, and a motor, wherein the annular cooling apparatus and the heating pipe are arranged in the tank body sequentially from inside to outside in a nested manner; the annular cooling apparatus includes a condensation inner wall, a condenser pipe, and a condensation outer wall that are arranged sequentially from inside to outside in a nested manner; a distillation chamber is formed between the heating pipe and the tank body, a condensation chamber is formed between the heating pipe and the condensation outer wall, and a hollow portion of the condensation inner wall forms a reaction chamber:

the motor electrically connects the heating pipe and the condensation inner wall and is able to drive the heating pipe and the condensation inner wall to rotate;

a feed inlet is configured at an end face of the tank body, and the end face is provided with a product discharge pipe connected to the reaction chamber and a condensated water outlet pipe connected to the condensation chamber; the other end face of the tank body away from the feed inlet is provided with a carboxylate feed pipe connected to the reaction chamber; the heating pipe is provided with a vapor outlet such that a water vapor is able to enter the condensation chamber from the distillation chamber; and an evaporation residue channel is configured at an end of the heating pipe away from the fed inlet, and the evaporation residue channel does not contact the annular cooling apparatus and communicates with the reaction chamber.

Optionally, in the above-mentioned device, the heating pipe is in a shape of a circular truncated cone, and a diameter of one end of the heating pipe close to the feed inlet is greater than a diameter of the other end of the heating pipe.

Optionally, int the above-mentioned device, a plurality of outer partitions are uniformly arranged on an outer wall of the heating pipe, and a plurality of an inner partition are arranged on an inner wall of the heating pipe at positions that correspond to the plurality of outer partitions; the outer partitions and the inner partitions each have a consistent length with the heating pipe; and an outer edge of each of the outer partitions abuts against the tank body, and an outer edge of each of the inner partitions abuts against the condensation outer wall.

Optionally, in the above-mentioned device, a plurality of vapor outlets are configured in the middle of sub-zones of the heating pipe divided by each of the outer partitions and each of the inner partitions, respectively; and a diameter of an end of each of the plurality of vapor outlets towards the tank body is greater than a diameter of an end towards the condensation outer wall.

Optionally, in the above-mentioned device, the plurality of vapor outlets are configured in a same plane perpendicular to a generatrix direction of the heating pipe; and a plurality of semi-annular isolation zones each are provided on the condensation outer wall at position corresponding to each of the plurality of vapor outlets.

Optionally, in the above-mentioned device, the evaporation residue channel is configured at an end away from the feed inlet of each of the sub-zones of the heating pipe divided by each of the outer partitions and each of the inner partitions, an opening of the evaporation residue channel is strip-shaped, and a position of an end of the sub-zone at which the evaporation residue channel is located is opposite to a preset rotation direction of the heating pipe.

Optionally, in the above-mentioned device, the inner wall of the heating pipe is provided with a spiral outer guide wire configured to guide condensated water into the condensated water outlet pipe.

Optionally, in the above-mentioned device, the condensation inner wall is provided with a spiral inner guide wire configured to guide a mixture of an evaporation residue and a carboxylic anhydride into the product discharge pipe.

Optionally, in the above-mentioned device, the tank body, the heating pipe, and the annular cooling apparatus are coaxially arranged.

According to another aspect of the present disclosure, a method for preparing a sucrose-6-ester is provided, wherein the method is implemented by the device described above, and comprises:

speration of reaction solution; starting the motor and the annular cooling apparatus, setting the heating pipe to a preset temperature, and feeding a reaction solution from the feed inlet of the tank body, such that the reaction solution is separated into an evaporation residue and a water vapor in the distillation chamber; allowing the evaporation residue to flow into the evaporation residue channel; and allowing the water vapor to enter the condensation chamber from the vapor outlet and be condensated into liquid water, and allowing the liquid water to flow out through the condensated water outlet pipe, wherein the reaction solution includes sucrose, an aprotic polar solvent, and an organotin esterification accelerator; and esterification reaction: subjecting the evaporation residue entering the reaction chamber through the evaporation residue channel to an esterification reaction with a carboxylic anhydride entering through the carboxylate feed pipe under preset conditions to obtain a sucrose-6-ester-containing solution.

In summary, the present disclosure has the following beneficial effects:

The condensation apparatus and the distillation apparatus are arranged together in a nested manner, and the distillation chamber, the condensation chamber, and the reaction chamber are sequentially formed from outside to inside. After entering the device from the distillation chamber, a reaction solution is gradually separated into a water vapor and an evaporation residue in the distillation chamber with the rotation of the heating pipe; under the action of gravity, the water vapor enters the condensation chamber from the vapor outlet and then is condensed and discharged; and the evaporation residue enters the reaction chamber, quickly reaches a temperature required by an esterification reaction due to a cooling effect of the condensation inner wall, and then undergoes an esterification reaction with a carboxylic anhydride entering the reaction chamber to produce a target product sucrose-6-ester. The device of the present disclosure achieves the integration of distillation, cooling, mixing, and reaction steps of a preparation process of a sucrose-6-ester, such that raw materials can be continuously fed into the production device. The reaction solution separation and the esterification reaction steps are uninterrupted, such that a sucrose-6-ester can be continuously produced, which greatly shortens the production cycle and improves the production efficiency of the sucrose-6-ester. The device has a small overall volume, a small floor space, a simple structure, and strong economy and practicality, which avoids the use of a large amount of a gas or solvent vapor capable of removing water in raw material in the prior art and overcomes the defects in the prior art such as high time consumption caused by the fact that the second reaction mixture needs to be fed into another space and then mixed with a carboxylic anhydride.

The above illustration is merely a summary of the technical solutions of the present disclosure. In order to allow the technical means of the present disclosure to be understood clearly and implemented in accordance with the content of the specification and allow the above and other objectives, features, and advantages of the present disclosure to be clear and easy to understand, specific embodiments of the present disclosure are described below.

BRIEF DESCRIPTION OF THE DRAWINGS

By reading the detailed description of the following preferred embodiments, various other advantages and benefits will become apparent to those of ordinary skill in the art. The drawings are provided merely to illustrate the preferred embodiments, rather than to limit the present disclosure. Throughout the drawings, the same reference numerals represent the same component. In the drawings:

FIG. 5 shows a schematic diagram illustrating a material flowing direction in the device for preparing a sucrose-6-ester when used to prepare a sucrose-6-ester according to an embodiments of the present disclosure; and FIG. 6 shows a schematic flow chart of a method for preparing a sucrose-6-ester according to an embodiment of the present disclosure.

DETAILED DESCRIPTION OF THE EMBODIMENTS

Exemplary embodiments of the present disclosure will be described in detail below with reference to the drawings. Although the drawings show exemplary embodiments of the present disclosure, it should be understood that the present disclosure may be implemented in various forms and should not be limited to the embodiments set forth herein. Instead, these embodiments are provided to provide a thorough understanding for the present disclosure, and a scope of the present disclosure can be fully conveyed to those skilled in the art.

The concept of the present disclosure is as follows:

In the prior art, a reaction solution for preparing a sucrose-6-ester needs to first undergo moisture removal using, a vapor or solvent in a reactor, and then is pressed into another reactor to react with a carboxylic anhydride to prepare the sucrose-6-ester. In the above process, the moisture removal using the vapor or solvent requires a high energy consumption, bulky equipment, and a large floor space, and can only lead to insufficient moisture removal after the moisture removal, the reaction solution also needs to be pressed into another reactor to undergo an esterification reaction, which requires additional energy and time and reduces the production efficiency of the sucrose-6-ester; and the production mode in the prior art is discontinuous, and the next reaction can only be conducted after the previous reaction is completed, which also seriously affects the production efficiency of the sucrose-ester.

Figure 1:
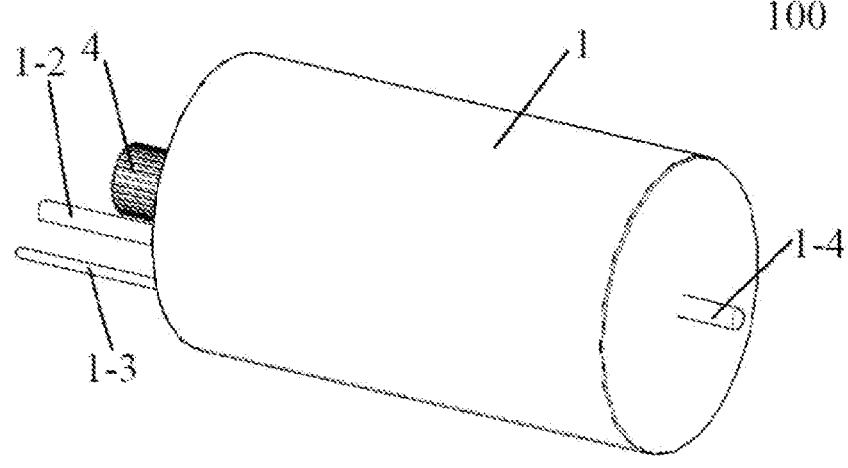
FIG. 1 shows a schematic diagram of an external overall structure of a device for preparing a sucrose-6-ester according to an embodiment of the present disclosure.
Figure 2:
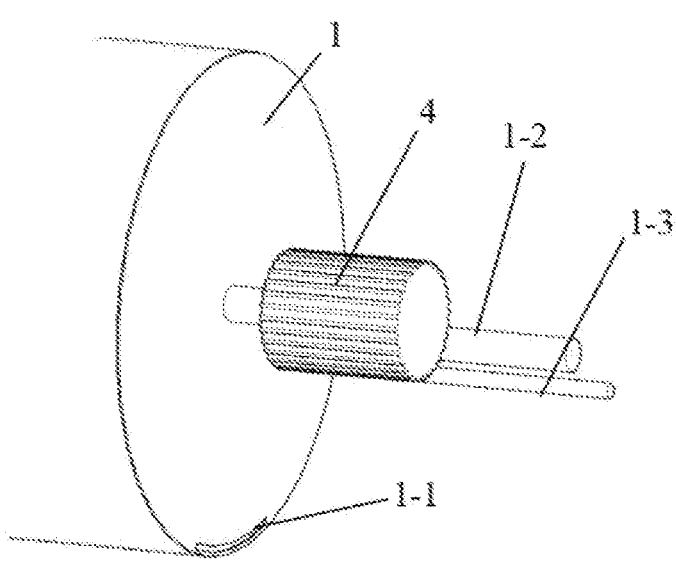
FIG. 2 shows a schematic structural diagram of an end face of a device for preparing a sucrose-6-ester according, to an embodiment of the present disclosure.
Figure 3:
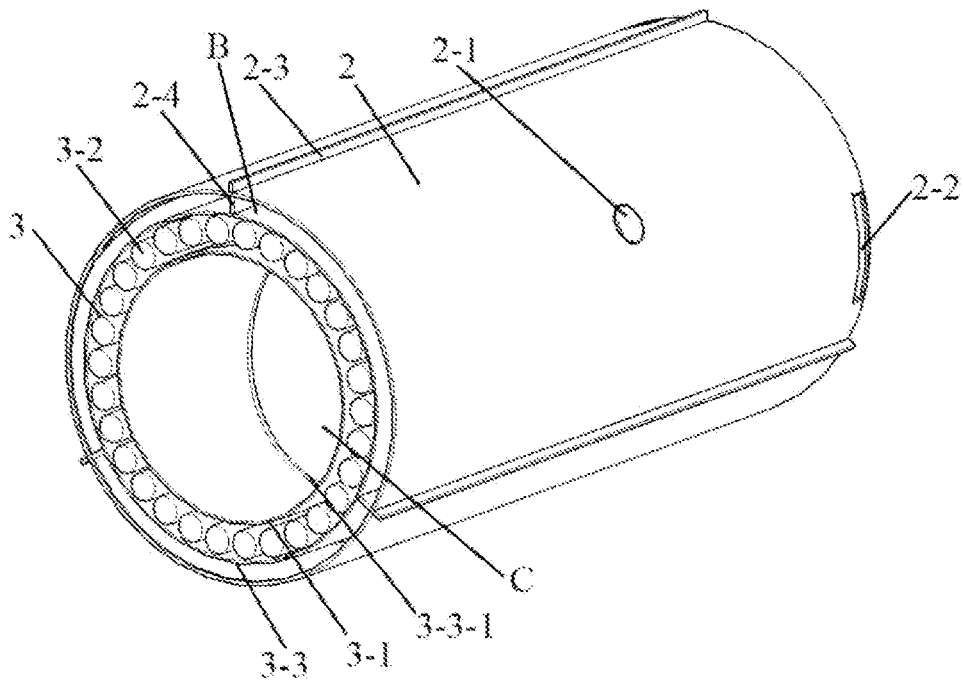
FIG. 3 shows a schematic structural diagram of an annular cooling apparatus arranged in a nested manner in the heating pipe of a device for preparing a sucrose-6-ester according to an embodiment of the present disclosure.
Figure 4:
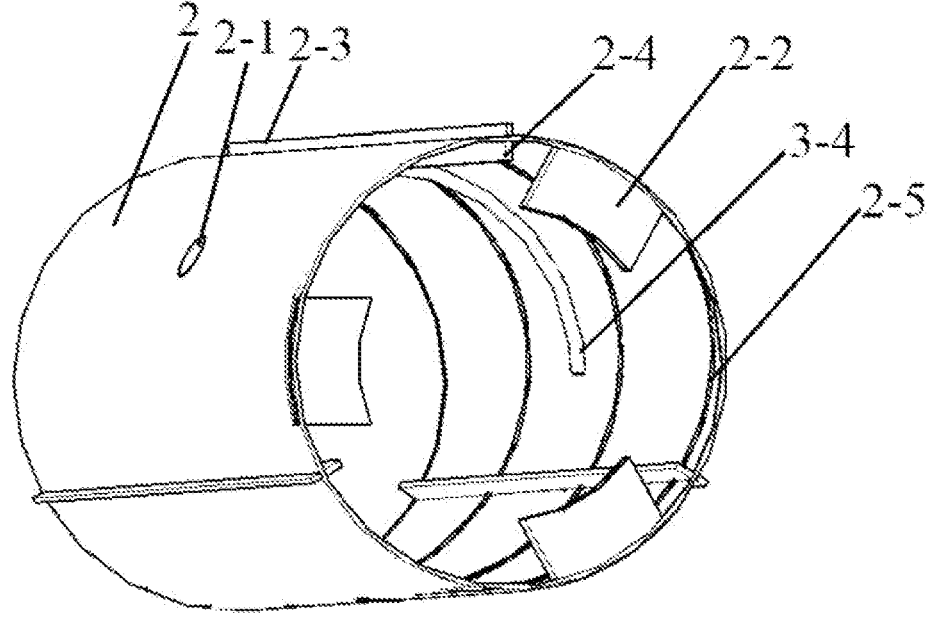
FIG. 4 shows a schematic diagram illustrating a working state of a heating pipe of a device for preparing a sucrose-6-ester at a specified time point according to an embodiment of the present disclosure.

FIG. 1 shows a schematic diagram of an external overall structure of a device for preparing a sucrose-6-ester according to an embodiment of the present disclosure; FIG. 2 shows a schematic structural diagram of an end face of a device for preparing a sucrose-6-ester according to an embodiment of the Present disclosure; FIG. 3 shows a schematic structural diagram of an annular cooling apparatus arranged in a nested manner in the heating pipe of a device for preparing a sucrose-6-ester according to an embodiment of the present disclosure; and FIG. 4 shows a schematic diagram illustrating a working state of a heating pipe of a device for preparing a sucrose-6-ester at a specified time point according to an embodiment of the present disclosure.

As shown in FIG. 1 to FIG. 4, the device 100 for preparing a sucrose-6-ester includes a tank body 1, a heating pipe 2, an annular cooling apparatus 3, and a motor 4, wherein the annular cooling device 3 and the heating pipe 2 are arranged in the tank body 1 sequentially from inside to outside in a nested manner; the annular cooling apparatus 3 includes a condensation inner wall 3-1, a condenser pipe 3-2, and a condensation outer wall 3-3 that are arranged sequentially from inside to outside in a nested manner; a distillation chamber is formed between the heating pipe 2 and the tank body 1, a condensation chamber B is formed between the heating pipe 2 and the condensation outer wall 3-3, and a hollow portion of the condensation inner wall 3-1 forms a reaction chamber C;

the motor 4 electrically connects the heating pipe 2 and the condensation inner wall 3-1 and is able to drive the heating pipe 2 and the condensation inner wall 3-1 to rotate;

a feed inlet 1-1 is configured at an end face of the tank body 1, and the end face is provided with a product discharge pipe 1-2 connected to the reaction chamber C and a condensated water outlet pipe 1-3 connected to the condensation chamber B; the other end face of the tank body away from the feed inlet is provided with a carboxylate feed pipe 1-4 connected to the reaction chamber C; the heating pipe 2 is provided with a vapor outlet 2-1 such that a water vapor is able to enter the condensation chamber B from the distillation chamber; and an evaporation residue channel 2-2 is configured at an end of the heating pipe 2 away % from the feed inlet, and the evaporation residue channel 2-2 does not contact the annular cooling apparatus 3 and communicates with the reaction chamber C.

As shown in FIC. 1 and FIG. 2, the device 100 for preparing a sucrose-6-ester is a tank body 1 from the outside, and one end face of the tank body 1 is provided with a product discharge pipe 1-2, a condensated water outlet pipe 1-3, and a feed inlet 1-1; and the other end face of the tank body 1 is provided with a carboxylate feed pipe 1-4. The motor 4 may be arranged at any end face of the tank body, as long as the motor does not interfere with other components of the device. In this embodiment, the motor 4 is arranged at the end face with the feed inlet 1-1.

It can be seen from FIG. 3 that the annular cooling apparatus 3 includes a condensation inner wall 3-1, a condenser pipe 3-2, and a condensation outer wall 3-3 that are arranged sequentially from inside to outside in a nested manner. The condenser pipe 3-2 can accommodate any condensation medium in the prior art, such as water and air; the condenser pipe may be distributed axially along the condensation inner wall 3-1 and the condensation outer wall 3-3 as shown in FIG. 2, or can spirally hover between the condensation inner wall 3-1 and the condensation outer wall 3-3, which is not limited in the present disclosure. In some embodiments, in order to achieve a better condensation effect, the condenser pipe 3-2 is arranged in close contact with the condensation inner wall 3-1 and the condensation outer wall 3-3.

As shown in FIG. 3, a radius of the condensation outer wall 3-3 is smaller than a radius of the heating pipe 2, and a radius of the heating pipe 2 is smaller than a radius of the tank body 1. Therefore, a chamber is formed between the condensation outer wall 3-3 and an inner wall of the heating pipe 2, which is called a condensation chamber B herein; another chamber is formed between an outer wall of the heating pipe 2 and the tank body 1, which is called a distillation chamber herein (not shown in the figures); and a hollow portion in the condensation inner wall is called a reaction chamber C herein. According to different functions of the chambers, feed and discharge pipes with different functions penetrating through end faces of the tank body 1 are connected to these chambers, respectively. Specifically, a feed inlet 1-1 is configured at an end face of the tank body 1, and the end face is provided with a product discharge pipe 1-2 connected to the reaction chamber C and a condensated water outlet pipe 1-3 connected to the condensation chamber B; and the other end face of the tank body away from the feed inlet is provided with a carboxylate feed pipe 1-4 connected to the reaction chamber C. As shown in FIG. 4, in some embodiments of the present disclosure, in order to control a feed speed of a reaction solution, the feed port 1-1 may be arranged in a long strip shape with a specified arc.

As shown in FIG. 3 and FIG. 4, the heating pipe 2 is provided with at least one vapor outlet 2-1 to connect the distillation chamber and the condensation chamber. A reaction solution undergoes distillation in the distillation chamber to obtain a water vapor and an evaporation residue; and the water vapor enters the condensation chamber 1B from the vapor outlet 2-1 and is further condensated into liquid water in the condensation chamber, and the liquid water enters the condensated water outlet pipe and then is discharged outside the device.

As shown in FIG. 3 and FIG. 4, an evaporation residue channel 2-2 is configured at an end of the heating pipe 2 away from the feed inlet, and the evaporation residue channel 2-2 does not contact the annular cooling apparatus 3 and communicates with the reaction chamber C.

An inlet of the evaporation residue channel 2-2 is configured at an end of the heating pipe away from the feed inlet 1-1 and extends in a radial direction of the heating pipe 2 to the reaction chamber. In this way, after entering from the feed inlet 1-1, a reaction solution gradually reaches the evaporation residue channel 2-2 with the rotation of the heating pipe 2, and because there is a specified distance between the feed inlet 1-1 and the evaporation residue channel 2-2, the moisture in the reaction solution will be evaporated and removed during the above process.

It should be noted herein that the evaporation residue channel 2-2 and the annular cooling apparatus 3 does not contact each other. In some embodiments of the present disclosure, a length of the annular cooling apparatus 3 may be slightly smaller than a length of the heating pipe 2 to reserve a position of the evaporation residue channel 2-2; and the evaporation residue channel 2-2 does not affect the rotation of the condensation inner wall 3-1.

As shown in FIG. 5, an entire operation process of the device can be briefly described as follows: The motor 4 electrically connects the heating pipe 2 and the condensation inner wall 3-1, and is able to drive the heating pipe 2 and the condensation inner wall 3-1 to rotate. A reaction solution, forming from a raw material solution for preparing a sucrose-6-ester that includes but not limited to sucrose, an aprotic polar solvent, and an organotin esterification accelerator, can be pumped into the device from the feed inlet 1-1. The motor 4 drives the heating pipe 2 to rotate, and the reaction solution in the distillation chamber is gradually thinned and stretched and tumbled forward with the rotation of the heating pipe 2. When the reaction solution is rotated to the side of the device close to the ground, most of the moisture in the reaction solution has been evaporated into gaseous water, at which point, the reaction solution tends to be closer the side of the device close to the ground due to gravity, and the gaseous water rises and will enter the condensation chamber from the vapor outlet 2-1. With the rotation of the heating pipe, the reaction solution is transformed to an evaporation residue, and under the action of gravity, the evaporation residue gradually enters the evaporation residue channel 2-2, and flows into the reaction chamber, is cooled on the condensation inner wall to reach a preset temperature of the esterification reaction, and undergoes an esterification reaction with a carboxylic anhydride entering the carboxylate feed pipe 1-4 to prepare the target product sucrose-6-ester.

In some embodiments of the present disclosure, in order to improve the overall stability of the device, the tank body 1, the heating pipe 2, and the annular cooling apparatus 3 can be coaxially arranged.

In some embodiments of the present disclosure, in order to make the evaporation residue more easily introduced into the evaporation residue channel 2-2, the heating pipe 2 may be arranged in a shape of a circular truncated cone, and a diameter of one end of the heating pipe close to the feed inlet 1-1 is greater than a diameter of the other end of the heating pipe. Since there is a specified potential difference between the feed inlet 1-1 and the inlet of the evaporation residue channel 2-2, the evaporation residue is easy to enter the evaporation residue channel 2-2.

As shown in FIG. 3, in some embodiments of the present disclosure, a plurality of outer partitions 2-3 are uniformly arranged on an outer wall of the heating pipe 2, and a plurality of inner partitions 2-4 are provided on an inner wall of the heating pipe 2 at positions that correspond to the plurality of outer partitions 2-3; the outer partitions 2-3 and the inner partitions 2-4 each have a consistent length with the heating pipe 2; and an outer edge of each of the outer partitions 2-3 abuts against the tank body 1, and an outer edge of each of the inner partitions 2-4 abuts against the condensation outer wall 3-3.

That is, the inner and outer partitions can be arranged correspondingly to divide the inner and outer walls of the heating pipe 2 into sub-zones with an equal size, and the distillation chamber and condensation chamber each are accordingly divided into a plurality of sub-chambers. The division of each chamber is conducive to the efficient use of the entire device.

As shown in FIG. 3 and FIG. 4, in some embodiments of the present disclosure, one or more vapor outlets 2-1 are configured in the middle of sub-zones of the heating pipe 2 that are formed through the division of the outer partitions and the inner partitions, and it is recommended to arrange two or more vapor outlets. These vapor outlets 2-1 are provided to make the distillation chamber communicate with the condensation chamber B, such that a water vapor generated in the distillation chamber can enter the condensation chamber B through the vapor outlets 2-1 in some embodiments of the present disclosure, in order to prevent a water vapor from flowing back to the distillation chamber from the condensation chamber B, a diameter of an end of each of the vapor outlets 2-1 towards the tank body 1 is greater than a diameter of an end towards the condensation outer wall 3-3. It should be noted that the heating pipe 2 may have a specified thickness, such that each vapor outlet 2-1 can be arranged in a shape of a circular truncated cone, and a diameter of an end towards the tank body 1 is greater than a diameter of an end towards the condensation outer wall 3-3; the heating pipe 2 may also be made from a relatively-thin material with thermal conductivity, such that each vapor outlet 2-1 can be arranged in a round-like truncated cone, a diameter of an end towards the tank body 1 is larger while a diameter of an end towards the condensation outer wall 3-3 is sharply reduced; and a generatrix of the round-like truncated cone can be an irregular line, such as a line with an inflection point.

As shown in FIG. 4, in some embodiments of the present disclosure, when a plurality of vapor outlets 2-1 are provided, the vapor outlets 2-1 are arranged in a same plane perpendicular to a generatrix direction of the heating pipe 2; that is, the plurality of vapor outlets 2-1 are radially distributed along a specified section of the heating pipe 2. Corresponding to positions of the plurality of vapor outlets 2-1, a plurality of semi-annular isolation zones 3-4 each are provided on the condensation outer wall 3-3 at positions corresponding to each of the plurality of vapor outlets 2-1. The semi-annular isolation zone 3-4 can be arranged at a side of the condensation outer wall 3-3 away from the ground. Because the condensation outer wall 3-3 is fixed, the semi-annular isolation zone 3-4 is also fixed relative to the ground, and the semi-annular isolation zone 3-4 is provided to block the vapor outlets 2-1 when rotating to the side away from the ground. With a sub-chamber of the distillation chamber as an example, when the sub-chamber rotates to the side away from the ground, a reaction solution or an evaporation residue in the sub-chamber cart flow into the condensation chamber from the vapor outlets under the action of gravity, in order to prevent this phenomenon, the semi-annular isolation zone 3-4 is provided at the side of the condensation outer wall 3-3 away from the ground, such that, when the sub-chamber rotates to a side close to the ground, that is, at a low point position of the entire travel, the vapor outlets 2-1 are unblocked, and the water vapor can enter the condensation chamber B; when the sub-chamber rotates to the side away from the ground (the position shown in FIG. 4), that is, at a high point position of the entire travel, the semi-annular isolation zone 3-4 blocks the vapor outlets 2-1 rotating to the side away from the ground, that is, the vapor outlets 2-1 are closed, and the reaction solution cannot enter the condensation chamber; and when the sub-chamber rotates to a position between the high point position and the low point position, a reaction solution or an evaporation residue flows downward, and whether the vapor outlets are closed will not affect the travel of the reaction solution or evaporation residue.

As shown in FIG. 4, in some embodiments of the present disclosure, an evaporation residue channel 2-2 is formed at an end away from the feed inlet 1-1 of each of the sub-zones of the heating pipe 2 that are formed through the division of the outer partitions 2-3 and the inner partitions 2-4, an opening of the evaporation residue channel 2-2 is strip-shaped, and a position of an end of the sub-zone at which the evaporation residue channel 2-2 is located is opposite to a preset rotation direction of the heating pipe 2. As shown in FIG. 3, a preset rotation direction of the heating pipe in FIG. 3 is a counterclockwise direction. Based on the angle of view in FIG. 3, a position of an end of each sub-zone away from the sight includes a side the same as the counterclockwise direction and a side opposite to the counterclockwise direction. In this embodiment, the evaporation residue channel is formed at the side opposite to the counterclockwise direction, such that, with the rotation of the heating pipe 2, an evaporation residue is easy to gradually enter the evaporation residue channel 2-2 and farther enter the reaction chamber under the action of gravity.

As shown in FIG. 4, in some embodiments of the present disclosure, the inner wall of the heating pipe 2 is provided with a spiral outer guide wire 2-5 configured to guide condensated water into the condensated water outlet pipe 1-3.

A condensation chamber is formed between the inner wall of the heating pipe 2 and the condensation outer wall 3-3. A water vapor is condensated into condensated water in the condensation chamber, and due to a drainage effect of the outer guide wire 2-5, the condensated water can flow smoothly into the condensated water outlet pipe 1-3 along the outer guide wire 2-5 and then discharged from the device.

As shown in FIG. 3, in some embodiments of the present disclosure, the condensation inner wall 3-1 is provided with a spiral inner guide wire 3-3-1 configured to guide a mixture of an evaporation residue and a carboxylic anhydride into the product discharge pipe 1-2. An evaporation residue and a carboxylic anhydride are mixed through the rotation of the condensation inner wall 3-1 and the action of the spiral inner guide wire 3-3-1, and under the action of the drainage of the inner guide wire 3-3-1, a resulting product flows into the product discharge pipe 1-2.

It should be noted that the overall size of the above device and a size of each component in the device are not limited and can be determined according to the needs of the reaction, such as a scale of the reaction and specific condition parameters of the reaction. Any reasonable sizes can be accepted, as long as the objective of the present disclosure can be achieved.

FIG. 6 shows a schematic flow chart of a method for preparing, a sucrose-6-ester according to an embodiment or the present disclosure. The method is implemented on the device described above, and at least includes the following steps S610 and S620:

reaction solution separation S610: the motor and the annular cooling apparatus are started, the heating pipe is set to a preset temperature, and a reaction solution is fed from the feed inlet of the tank body, such that the reaction solution is separated into an evaporation residue and a water vapor in the distillation chamber; the evaporation residue is allowed to flow into the evaporation residue channel; and the water vapor is allowed to enter the condensation chamber from the vapor outlet and be condensated into liquid water, and the liquid water is allowed to flow out through the condensated water outlet pipe, where the reaction solution includes sucrose, an aprotic polar solvent, and an organotin esterification accelerator; and esterification reaction S620: the evaporation residue entering the reaction chamber through the evaporation residue channel is subjected to an esterification reaction with a carboxylic anhydride entering through the carboxylate feed pipe under preset conditions to obtain a sucrose-6-ester-(containing solution.

In the above method, there is no limitation on rotational speeds of the heating pipe and the condensation inner wall in the present disclosure. In some embodiments of the present disclosure, a rotational speed of the heating pipe may be set in the range of 40 rpm to 200 rpm; and a rotational speed of the condensation inner wall may be set in the range of 40 rpm to 200 rpm. If the rotational speed of the heating pipe is lower than 40 rpm, an action force provided by rotation to a reaction solution is too small, such that the reaction solution cannot be evenly heated to evaporate the moisture, and the undesirable phenomenon of local overheating occurs; and if the rotational speed of the hating pipe is higher than 200 rpm, the rotational speed is too fast, and the motor should meet high requirements, which increases the device cost. If the rotational speed of the condensation inner wall is lower than 40 rpm, an action force provided by rotation to the evaporation residue and carboxylic anhydride is too small, such that the two cannot thoroughly mixed; and if the rotational speed of the condensation inner wall is higher than 200 rpm, the rotational speed is too fast, and the motor should meet high requirements, which increases the device cost.

The raw materials and preset conditions for the esterification reaction in the above method are not limited, which can refer to the prior art and can also lie adopted according to the following recommended technical solutions.

In the present disclosure, a type of the organotin compound is not limed, and a monotin organic compound or a hi-tin organic compound can be adopted. In some embodiments, the organotin compound is optionally any one or more selected from the group consisting of 1,3-hydrocarbyloxy-1,1,3,3-tetra-(hydrocarbyl)distannoxane, tin di(hydrocarbyl)oxide, 1,3-diacyloxy-1,1,3,3-tetra-(hydrocarbyl)distannoxane, and 1-diacyloxy-1,1,3,3-tetra-(hydrocarbyl) distannoxane; in some other embodiment, the organotin compound is 1,3-diacyloxy-1,1,3,3-tetra-(hydrocarbyl)distannoxane; and in some other embodiments, the organotin compound is 1,3-diacetoxy-1,1,3,3-tetrabutyldistannoxane. The hydrocarbyloxy is Optionally selected from the group consisting of alkoxy and phenoxy. In sore embodiments, the alkoxy is optionally selected from the group consisting of methoxy, ethoxy, n-propoxy, n-butoxy, n-pentyloxy, and n-hexoxy; and in some other embodiments, the alkoxy is methoxy. In some embodiments, the hydrocarbyl is optionally selected front the group consisting of alkyl, cycloalkyl, aryl, and aralkyl; in some other embodiments, the hydrocarbyl is alkyl; and in some other embodiments, the hydrocarbyl is n-butyl.

In the present disclosure, there is no limitation on a type of the aprotic polar solvent. In some embodiments, the aprotic polar solvent is any one or more selected from the group consisting of acetonitrile, 1,4-dioxane, methyl ethyl ketone (MEK), methyl isobutyl ketone (MIK), nitromethane, nitroethane, cyclohexanone, dimethyl sulfoxide (DMSO), N-methylpyrrolidone (NMP), N,N-dimethylacetamide (DMA), hexamethylphosphoramide (HMPA), and N-dimethylformamide (DMF); and in some other embodiments, the aprotic polar solvent is a acetonitrile.

In the present disclosure, there is no limitation on an amount of the aprotic polar solvent. In some embodiments, based on a mass of sucrose, a ratio of a mass of the solvent to the mass of sucrose is in the range of 2 to 20; in some other embodiments, the ratio of the mass of the solvent to the mass of sucrose is in the range of 3 to 10; and in some other embodiments, the ratio of the mass of the solvent to the mass of sucrose is in the range of 4 to 8.

In the present disclosure, there is no limitation on a eating temperature for the heating pipe. In some embodiments, the heating temperature may range from 65° C. to 150° C. and in some other embodiments, the heating temperature may range from 85° C. to 120° C.

In the present disclosure, the reaction chamber can also be provided with a vacuum pipe, and the vacuum pipe can be connected to a vacuum pump. When the vacuum pipe is connected to a vacuum pump, a negative pressure in the device is not limited. In some embodiments, the negative pressure in the device may be maintained at 0.01 kPa to 50 kPa; and in some other embodiments, the negative pressure in the device may be maintained at 0.5 kPa to 20 kPa.

In the present disclosure, there is no limitation on a type of the carboxylic anhydride, and the carboxylic anhydride is any one selected from the group consisting of acetic anhydride butyric anhydride, benzoic anhydride, stearic anhydride, and lauric anhydride and is preferably acetic anhydride. The above types of organic acid anhydrides lead to the corresponding sucrose-6-carboxylates sucrose-6-acetate, sucrose-6-butyrate, sucrose-6-benzoate, sucrose-6-fatty acid ester, and sucrose-6-laurate. The sucrose-6-acetate and sucrose-6-benzoate can be used as raw materials for synthesizing other sucrose-6-carboxylates and can also be used as intermediates for synthesizing a sweetener sucralose; and the other types of sucrose-6-carboxylate can be used as food additives, chemical products, and synthetic intermediates for other reactions.

In the present disclosure, there is no limitation on an amount of the carboxyli anhydride, in some embodiments, based on the mass of sucrose, a ratio of a mass of the carboxylic anhydride to the mass of the sucrose is 0.6 to 3.0; and in some other embodiments, the ratio of the mass of the carboxylic anhydride to the mass of the sucrose is 0.8 to 1.

In the present disclosure, there is no limitation on the reaction conditions of the esterification reaction. In some embodiments, the esterification reaction may be conducted at the temperature of 0° C. to 50° C. and in some other embodiments, the esterification reaction may be conducted at the temperature of 1° C. to 20° C. In some embodiments, the esterification reaction may be conducted for 10 min to 24 h; and in some other embodiments, the esterification reaction may be conducted for 30 min to 4 h.

It should be noted that reaction conditions not detailed above may refer to the prior art.

Testing Methods and Reagent Sources Involved in the Present Disclosure

High-performance liquid chromatography (HPLC) (for testing the contents of substances in a reaction product such as sucrose and sucrose-6-ester).

High-performance liquid chromatograph of Shimadzu, Japan: RID-10A differential refractive index detection, LC-10ADVP high-pressure pump, and CTO-10ASVP incubator: chromatographic column: Agilent XDB C18 column (250 m×4.6 mm, 5 μm); mobile phase: methanol-0.125% dipotassium phosphate (DKP) aqueous solution (4:6); column temperature: 30° C.; and flow rate: 1.0 mL/min. Methanol (chromatographically pure), DKP (analytically pure) ultrapure water (UPW), and sucralose (purity: 99.9%) are required, and a content is determined by an external standard method.

Moisture Test Method

A moisture content is determined by the Karl Fischer method, which can refer to the prior art and will not be repeated in various examples, Reagent Sources The chemical reagents involved in the present disclosure and raw materials for preparing a sucrose-6-ester may be commercially available, which are not limited in the present disclosure.

Example 1

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 300 kg of a reaction solution.

The device for preparing a sucrose-6-ester of the present disclosure was used to produce a sucrose-6-ester as follows: The motor and the annular cooling apparatus were started, the temperature of the heating pipe was set to 80° C., a rotational speed of the heating pipe was set to 100 rpm, and a rotational speed of the condensation inner wall was set to 100 rpm.

The reaction solution prepared above was continuously fed into the device through the feed inlet at a rate of 4 m³/h, and about 1 h later, it was expected that an evaporation residue had entered the reaction chamber, at which point a sample could be taken from the evaporation residue and tested for a moisture content. The moisture content in this example is lower than 500 ppm.

With a mass ratio of sucrose to acetic anhydride being 1:1.1, the acetic anhydride was introduced into the carboxylate freed pipe to allow an esterification reaction in the reaction chamberat about 10° C., and it took about 1 h from the beginning of nixing of the two to the final discharge of a reaction product from the reaction product discharge port; and a sucrose-6-ester-containing product flowing out of the reaction product discharge port was collected.

Water was added with a volume ratio of the water to the reaction solution being 0.25:1 to quench the reaction, and hexane was added with a volume ratio of the hexane to the reaction solution being 1:1 to extract the organotin esterification accelerator to obtain a sucrose-6-acetate solution. A content of each substance in the sucrose-6-acetate solution was analyzed by HPLC. The normalization below and in the following examples means that, when a mixture is subjected to separation assay by HPLC, a sum of all substances is specified as 100%, and a percentage of each substance to all substances is determined according to a peak area. The product distribution was as follows:

a. sucrose-6-acetate: 90.22% (normalized);

b. diacetate: 7.89% (normalized); and c. sucrose: 0.35% (normalized).

Example 2

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 500 hg of a reaction solution.

The device for preparing a sucrose-6-ester of the present disclosure was used to produce a sucrose-6-ester as follows: The motor and the annular cooling apparatus were started, the temperature of the heating pipe was set to 100° C., a rotational speed of the heating pipe was set to 150 rpm, and a rotational speed of the condensation inner wall was set to 100 rpm.

The reaction solution prepared above was continuously fed imo the device through the feed inlet at a rate of 6 m³/h, and about 1.5 h later, it was expected that an evaporation residue had entered the reaction chamber, at which point a sample could be taken from the evaporation residue and tested for a moisture content. The moisture content in this example is lower than 450 ppm.

With a mass ratio of sucrose to acetic anhydride being 1:1.1 the acetic anhydride was introduced into the carboxylate feed pipe to allow an esterification reaction in the reaction chamberat about 15° C., and it took about 1.5 h from the beginning of mixing of the two to the final discharge of a reaction product from the reaction product discharge port; and a sucrose-6-ester-containing product flowing out of the reaction product discharge port was collected.

Water was added with a volume ratio of the water to the reaction solution being 0.25:1 to quench the reaction, and hexane was added with a volume ratio of the hexane to the reaction solution being 1:1 to extract the organotin esterification accelerator to obtain a sucrose-6-acetate solution. A content of each substance in the sucrose-6-acetate solution was analyzed by HPLC. The product distribution was as follows:

a. sucrose-6-acetate: 89.70%. (normalized);

b. diacetate: 8.20% (normalized); and c. sucrose: 0.24% (normalized).

Example 3

Sucrose, an organotin esterification accelerator (1,1,3-diacetoxy-1,1,3,3-tetrabutyldistannoxane), and an aprotic polar solvent (DMF) were taken in a mass ratio of 1:2:10 and prepared into 500 kg of a reaction solution.

The device for preparing a sucrose-6-ester of the present disclosure was used to produce a sucrose-6-ester as follows: The motor and the annular cooling apparatus were started, the temperature of the heating pipe was set to 90° C., rotational speed of the heating pipe was set to 200 rpm, and a rotational speed of the condensation inner wall was set to 200 rpm.

The reaction solution prepared above was continuously fed into the device through the feed inlet at a rate of 8 m³/h, and about 1 h later, it was expected that an evaporation residue had entered the reaction chamber, at which point a sample could be taken from the evaporation residue and tested for a moisture content. The moisture content in this example is lower than 500 ppm.

With a mass ratio of sucrose to acetic anhydride being 1:1.1, the acetic anhydride was introduced into the carboxylate feed pipe to allow an esterification reaction in the reaction chamber at about 10° C., and it took about 1 h from the beginning of mixing of the two to the final discharge of a reaction product from the reaction product discharge port; and a sucrose-6-ester-containing product flowing out of the reaction product discharge port was collected.

Water was added with a volume ratio of the water to the reaction solution being 0.25:1 to quench the reaction, and hexane was added with a volume ratio of the hexane to the reaction solution being 1:1 to extract the organotin esterification accelerator to obtain a sucrose-6-acetate solution. A content of each substance in the sucrose-6-acetate solution was analyzed by HPLC. The product distribution was as follows:

a. sucrose-6-acetate: 88.90% (normalized);

b. diacetate: 8.05% (normalized); and c. sucrose: 0.20% (normalized).

Comparative Example 1

Sucrose, an organotin esterification accelerator (1,1,3-diacetoxy-1,1,3,3 tetrabutyldistannoxane), and an aprotic polar solvent (DMF) were taken in a mass ratio of 1:2:10 and prepared into 300 kg of a reaction solution, and the reaction solution was heated at 90° C. for dissolution to obtain a reaction mixed solution.

The reaction mixed solution was dehydrated by means of falling liquid in a packed tower. The packed tower has a diameter of 40 mm and was packed with a 3×8 glass spring packing at a packing height of 1 m, which is equivalent to 10-stage tower plates.

The reaction mixed solution prepared above was fed from an inlet at a top of the packed tower, with a negative pressure of 0.5 kPa; and a cyclohexane vapor (100° C., 4 atm) was fed from a flask gas inlet at a bottom of the packed tower. The reaction mixed solution and the cyclohexane vapor were in countercurrent contact to allow a reaction. A distillate (a vapor including cyclohexane, water, and DMF) discharged from the top of the packed tower was condensed, collected, dried to remove water, and then recycled.

A liquid sample was collected in a flask at the bottom of the packed tower, which was transparent and light-amber. A retention time of the reaction solution in a gas-liquid exchange reactor was about 1 min.

A sucrose content of a resulting solution was calculated to be 10%. The resulting solution was pressed into another reactor, then acetic anhydride was added dropwise at a temperature lower than 10° C. with a mass ratio of sucrose to acetic anhydride being 1:1.1 to allow an esterification reaction at a temperature lower than 10° C. for 2 h, and then water was added according to a ratio of 0.25:1 for quenching the reaction; and cyclohexane was added according to a ratio of 1:1 for extracting the organotin compound, and a resulting sucrose-6-acetate solution was analyzed by HPLC. Analysis results of the products were as follows:

a. sucrose-6~acetate: 72.05% (normalized);

b. diacetate: 4.36% (normalized); and c. sucrose: 22.76% (normalized),

It can be seen from Examples 1 to 3 and Comparative Example 1 that, compared with the packing and falling liquid device in Comparative Example 1, the device provided in the present disclosure can lead to a high sucrose-6-carboxylate yield, a low side reaction occurrence probability, and a complete sucrose reaction. It can be known that the sucrose-6-acetate yield can reach 90.20% (normalized) in some examples of the present disclosure, but is only 72.05 (normalized) in Comparative Example 1; that is, the sucrose-6-carboxylate yield in the present disclosure is significantly higher than that in the prior art. Similarly, front the diacetate and sucrose contents in the reaction products, it can be seen that the side reaction occurrence probability of the present disclosure is significantly reduced, and the conversion of sucrose in the present disclosure is more thorough.

In summary, the present disclosure has the following beneficial effects:

The condensation apparatus and the distillation apparatus are arranged together in a nested manner, and the distillation chamber, the condensation chamber, and the reaction chamber are sequentially formed from outside to inside. After entering the device from the distillation chamber, a reaction solution is gradually separated into a water vapor and an evaporation residue in the distillation chamber with the rotation of the heating pipe; under the action of gravity, the water vapor enters the condensation chamber from the vapor outlet and then is condensed and discharged; and the evaporation residue enters the reaction chamber, quickly reaches a temperature required by an esterification reaction due to a cooling effect of the condensation inner wall, and then undergoes an esterification reaction with a carboxylic anhydride entering the reaction chamber to produce a target product sucrose-6-ester. The device of the present disclosure achieves the integration of distillation, cooling mixing, and reaction steps of a preparation process of a sucrose-6-ester, such that raw materials can be continuously fed into the production device. The reaction solution separation and esterification reaction steps are uninterrupted, such that a sucrose-6-ester can be continuously produced, which greatly shortens the production cycle and improves the production efficiency of the sucrose-6-ester. The production device has a small overall volume, a small floor space, a simple structure, and Strong economy and practicability, which avoids the use of a large amount of a gas or solvent vapor capable of removing water in raw materials in the prior art and overcomes the defects in the prior art such as high time consumption caused by the fact that the second reaction mixture needs to be pressed into another space and then mixed with a carboxylic anhydride. The above are merely specific embodiments of the present disclosure, and under the above instruction of the present disclosure, those skilled in the art may make other improvements or variations on the basis of the above examples. It should be understood for those skilled in the art that the above specific description is merely intended to well explain the purpose of the present disclosure, and a protection scope of the present disclosure shall be subject to the protection scope of the claims.

In addition, those skilled in the art can understand that, although some embodiments herein include some features included in other embodiments but no other features, a combination of features of different embodiments' falls within the scope of the present disclosure and forms a different embodiment. For example, in the claims, any one of the claimed embodiments can be used in any combination.

What is claimed is:

1. A device for preparing a sucrose-6-ester, comprising a tank body, a heating pipe, an annular cooling apparatus, and a motor, wherein the annular cooling apparatus and the heating pipe are arranged in the tank body sequentially from inside to outside in a nested manner; wherein the annular cooling apparatus comprises a condensation inner wall, a condenser pipe, and a condensation outer wall that are arranged sequentially from inside to outside in a nested manner; a distillation chamber is formed between the heating pipe and the tank body, a condensation chamber is formed between the heating pipe and the condensation outer wall, and a hollow portion of the condensation inner wall forms a reaction chamber;

the motor electrically connects to the heating pipe and the condensation inner wall, and is able to drive the heating pipe and the condensation inner wall to rotate;

a feed inlet connected to the distillation chamber is configured at an end face of the tank body, and the end face is further provided with a product discharge pipe connected to the reaction chamber and a condensed water outlet pipe connected to the condensation chamber; the other end face of the tank body away from the feed inlet is provided with a carboxylate feed pipe connected to the reaction chamber; the heating pipe is provided with a vapor outlet such that a water vapor is able to enter the condensation chamber from the distillation chamber; and an evaporation residue channel is configured at an end of the heating pipe away from the feed inlet, and the evaporation residue channel does not contact the annular cooling apparatus and communicates with the reaction chamber; and a plurality of vapor outlets are configured in a same plane perpendicular to a generatrix direction of the heating pipe; and a plurality of semi-annular isolation zones each are provided on the condensation outer wall at positions corresponding to each of the plurality of vapor outlets.

2. The device according to claim 1, wherein the heating pipe is in a shape of a circular truncated cone, and a diameter of one end of the heating pipe close to the feed inlet is greater than a diameter of the other end of the heating pipe.

3. The device according to claim 1, wherein a plurality of outer partitions are uniformly arranged on an outer wall of the heating pipe, and a plurality of inner partitions are arranged on an inner wall of the heating pipe at positions that correspond to the plurality of outer partitions; the outer partitions and the inner partitions each have a consistent length with the heating pipe; and an outer edge of each of the outer partitions abuts against the tank body, and an outer edge of each of the inner partitions abuts against the condensation outer wall.

4. The device according to claim 3, wherein the plurality of vapor outlets are configured in the middle of sub-zones of the heating pipe divided by each of the outer partitions and each of the inner partitions, respectively; and a diameter of an end of each of the plurality of vapor outlets towards the tank body is greater than a diameter of an end towards the condensation outer wall.

5. The device according to claim 1, wherein the inner wall of the heating pipe is provided with a spiral outer guide wire configured to guide condensed water into the condensed water outlet pipe.

6. The device according to claim 1, wherein the condensation inner wall is provided with a spiral inner guide wire configured to guide a mixture of an evaporation residue and a carboxylic anhydride into the product discharge pipe.

7. The device according to claim 1, wherein the tank body, the heating pipe, and the annular cooling apparatus are coaxially arranged.

8. A method for preparing a sucrose-6-ester, wherein the method is implemented by the device according to claim 1, and comprises:

separation of reaction solution: starting the motor and the annular cooling apparatus, setting the heating pipe to a preset temperature, and feeding the reaction solution from the feed inlet of the tank body, such that the reaction solution is separated into an evaporation residue and the water vapor in the distillation chamber; allowing the evaporation residue to flow into the evaporation residue channel; and allowing the water vapor to enter the condensation chamber from the vapor outlet and be condensed into liquid water, and allowing the liquid water to flow out through the condensed water outlet pipe, wherein the reaction solution comprises sucrose, an aprotic polar solvent, and an organotin esterification accelerator; and esterification reaction: subjecting the evaporation residue entering the reaction chamber through the evaporation residue channel to an esterification reaction with a carboxylic anhydride entering through the carboxylate feed pipe under preset conditions to obtain a sucrose-6-ester-containing solution.

9. The device according to claim 2, wherein the tank body, the heating pipe, and the annular cooling apparatus are coaxially arranged.

10. The device according to claim 3, wherein the tank body, the heating pipe, and the annular cooling apparatus are coaxially arranged.

11. The device according to claim 4, wherein the tank body, the heating pipe, and the annular cooling apparatus are coaxially arranged.

12. The device according to claim 5, wherein the tank body, the heating pipe, and the annular cooling apparatus are coaxially arranged.

13. The device according to claim 6, wherein the tank body, the heating pipe, and the annular cooling apparatus are coaxially arranged.

* * * * *